United States Patent [19]

Shaw et al.

[11] Patent Number: 5,037,613
[45] Date of Patent: Aug. 6, 1991

[54] INCUBATOR

[75] Inventors: James D. Shaw, Hilton; Martin F. Muszak, Rochester, both of N.Y.

[73] Assignee: Eastman Kodak Company, Rochester, N.Y.

[21] Appl. No.: 324,121

[22] Filed: Mar. 16, 1989

[51] Int. Cl.⁵ .............................................. G01N 35/00
[52] U.S. Cl. .......................................... 422/64; 436/46
[58] Field of Search ................ 422/63, 64, 72; 436/43, 436/45, 46

[56] References Cited

U.S. PATENT DOCUMENTS 4,296,069  10/1987  Smith et al. ............................ 422/64
4,298,571  11/1981  DiFulvio et al. ....................... 422/65
4,406,547   9/1983  Aihara .................................... 422/64

FOREIGN PATENT DOCUMENTS 61-259142  11/1986  Japan .

Primary Examiner—Robert J. Warden
Assistant Examiner—D. John Griffith, Jr.
Attorney, Agent, or Firm—Dana M. Schmidt

[57] ABSTRACT

There is described an incubator comprising a rotor moving above a stationary surface, the rotor comprising stations having a cover member, a lower support for a test element, and a spring biasing the cover member against the lower support. In one aspect of the invention, three reference surfaces are provided in the stationary surface for the lower support of the rotor to slide against. In another aspect, an improved spring is provided for ready, releasible capture by the rotor.

7 Claims, 4 Drawing Sheets

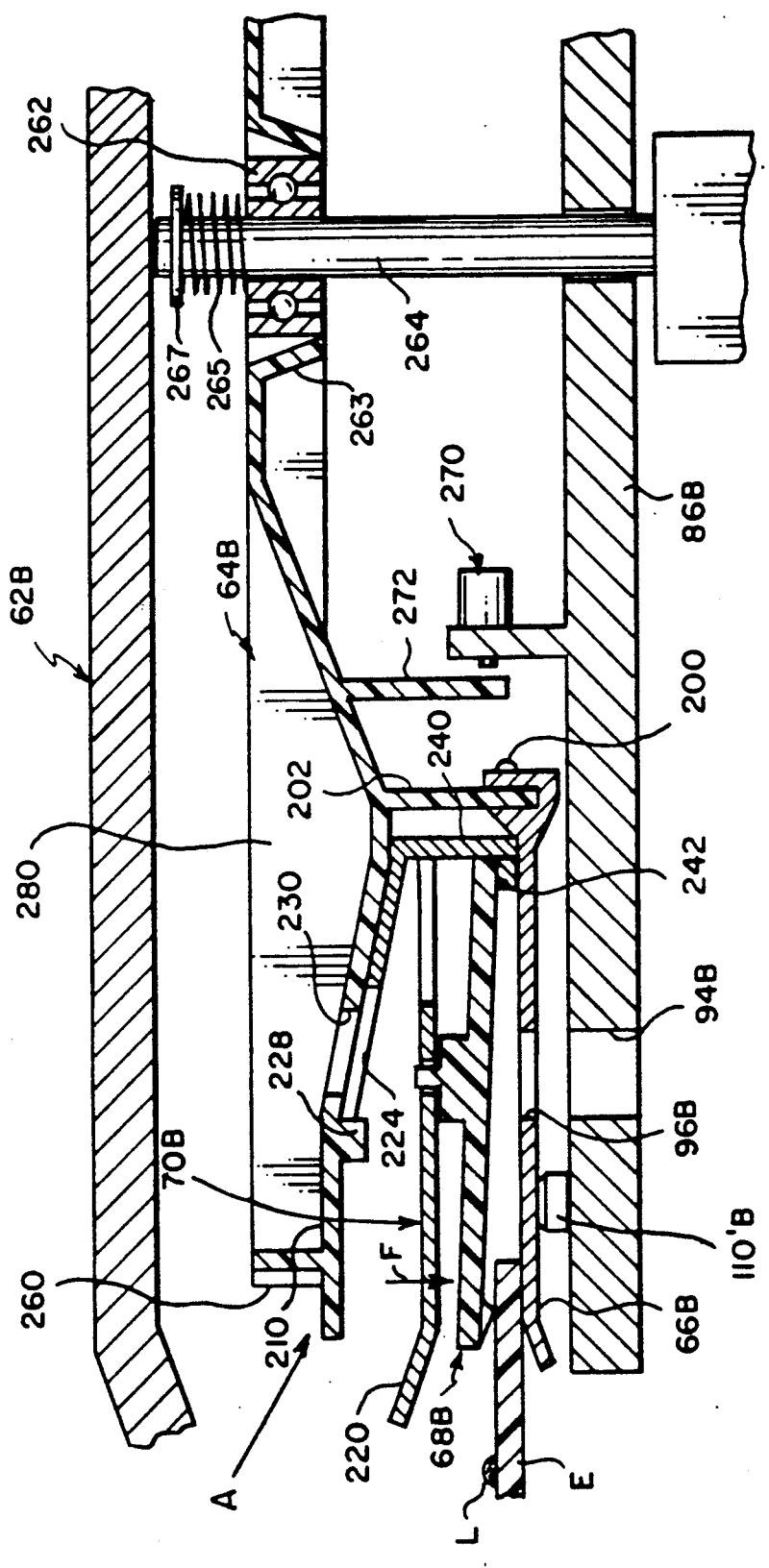

INCUBATOR

FIELD OF THE INVENTION

This invention relates to incubators used in analyzers to assay for analytes in liquids.

BACKGROUND OF THE INVENTION

Certain analyzer incubators, such as those shown in U.S. Pat. No. 4,298,571, comprise a rotor that is an annular disk that has a lower support surface for test elements and an evaporation cover at each station around the circumference of the disk. (The specific incubator shown in the '571 patent is for potentiometric test elements, but a similar one has been used for colorimetric test elements in commercial instruments.) The entire disk is cast as a single piece, necessitating castings of the finest quality, in order to ensure that each support surface (for each test element) is flat and at a predictable height in the "Z" dimension. That is, little or no warpage is tolerated. The reason for the strict control of height tolerances is that for some incubators, the test elements held on such support surfaces, are read in place at the respective incubator station by a built-in reflectometer, particularly for those incubators requiring multiple readings of the same test elements (the so-called "rate" test elements). Any variation in height (the Z dimension) of the support surface away from its predictable location, called a "processing" error due to the disc wobbling as it rotates, alters the amount of light falling onto the test element from the reflectometer. This in turn creates an error in the colorimetric reading.

It is known that rate test elements are read at the first derivative level, so that errors introduced into the absolute readings disappear. However, some test elements are colorimetrically read only at their end point. If the same incubator is to be used for both rate test elements and such end-point elements, a desired goal to simplify analyzers, an improvement is needed in the rotor to avoid the noted precessing error.

Not only does such needed accuracy in reading cause manufacturing problems in making such rotors, but in addition, the rotors are very expensive. This leads to a substantial loss if such rotors are defective or break for any reason.

Yet another drawback with the rotors of the '571 patent is that the test element holding means is not readily removable from the rotor, due to the manner in which the hold-down spring is attached.

There has been a need, therefore, prior to this invention, to provide an incubator in which the rotor provides support surfaces that more readily insure a predictable height of test elements from the surface on which the rotor rotates, without requiring careful production of the entire rotor; or a more readily removable test element holding means.

One solution to this problem has been to provide a rotor that has no supporting surface underneath the test elements, which instead pushes test elements around directly on a stationary incubator surface. Examples are shown in, e.g., Japanese Kokai 86/259142. For low-throughput volumes, such is not a problem. However, high-throughput analyzers rotate the rotors very rapidly, with considerable acceleration. If, as is common, the test element is manufactured from a plastic material such as polystyrene that does not wear well, there is considerable polystyrene dust created that jams up the incubator, requiring repeated cleaning.

Thus, the need for an improved rotor has remained unmet, at least regarding high-throughput analyzers. (As used herein, high-throughput means at least 200 test elements per hour.)

SUMMARY OF THE INVENTION

We have constructed an incubator useful for high through-put analyzers that avoids the need for expensive lower supports in the rotor.

More specifically, in accord with one aspect of the invention, there is provided an incubator for use in an analyzer, the incubator comprising a stationary incubator surface above which test elements are moved while being held in assigned test element stations; a rotor including holding means for holding test elements at the stations; means for rotating the rotor about an axis, including drive means and means for connecting the rotor to the drive means, the connecting means including bearing means for providing relative rotation between the rotor and the stationary surface; the holding means including a lower support mounted to slide above the stationary surface and a cover member, a test element being sandwichable between the lower support and the cover member; and reading means fixed in the incubator for scanning a test element held in the holding means, one of the lower support and the cover member being apertured to allow a scanning beam to pass through to a test element held by the holding means. The incubator is improved in that the stationary surface includes three reference surfaces comprising a fraction of the stationary surface and positioned a predetermined distance along the axis, the reference surface being circumferentially positioned adjacent the light beam to insure proper reading distance for test elements read by the reading means, and wherein the bearing means is free to move in a direction parallel to the axis, whereby the reference surfaces and not the bearing means determine the distance along the axis of test elements held by the holding means at the read station.

In accord with another aspect of the invention, there is provided an incubator for use in an analyzer, the incubator comprising a stationary incubator surface above which test elements are moved while being held in assigned test element stations; a rotor including holding means for holding test elements at the stations; means for rotating the rotor about an axis, including drive means and means for connecting the rotor to the drive means; the holding means including a lower support mounted to slide above the stationary surface and a cover member, a test element being sandwichable between the lower support and the cover member; and the rotor including a spring biasing the cover member towards the lower support. The incubator is improved in that the spring is a leaf spring having a body portion releasibly pressed against the cover member, and two legs extending from the body portion.

Thus, it is an advantageous feature of this invention that an incubator is provided with an inexpensive rotor for high through-put, which automatically corrects for precessing errors without necessitating careful rotor manufacturing.

Another advantageous feature is the use of element holding means that are readily removable from the incubator.

Other advantageous features will become apparent upon reference to the following detailed description, when read in light of the attached drawings.

BRIEF DESCRIPTION OF THE DRAWINGS

FIG. 6 is an elevational view similar to FIG. 4, but illustrating an alternate embodiment;

DESCRIPTION OF THE PREFERRED EMBODIMENTS

Figure 1:
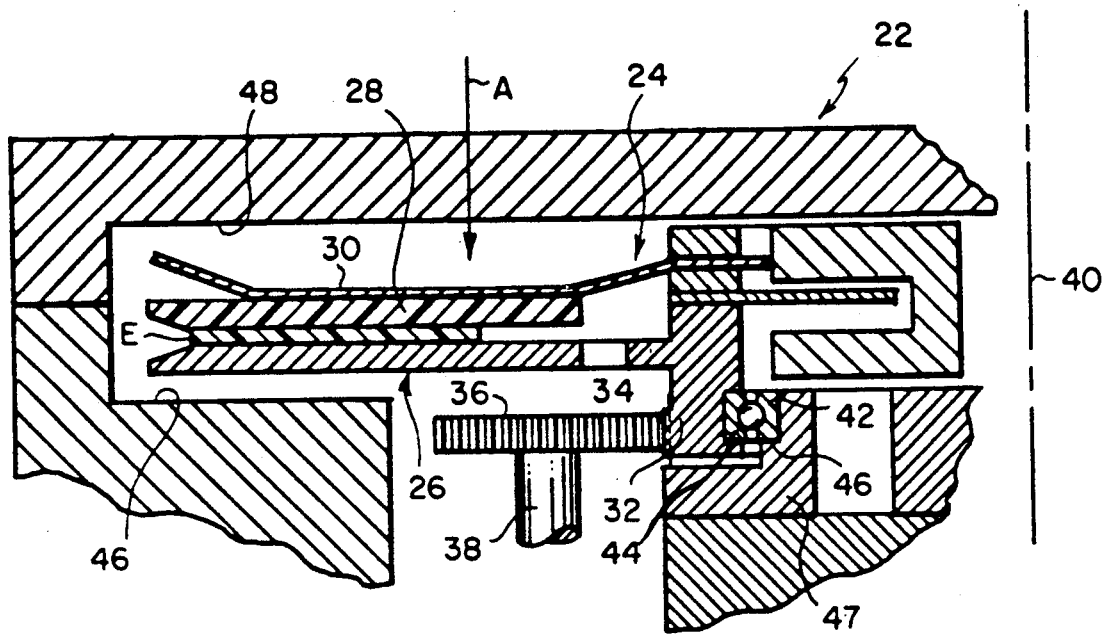
FIG. 1 is a fragmentary elevational view in section of an incubator constructed in accordance with the prior art.

The invention is described in connection with certain preferred embodiments wherein the incubator has a rotor constructed with various features, as part of a blood analyzer, to allow a test element to be read with a light beam while in the incubator. In addition the invention is useful in any high through-put incubator, whether it is an integral part of an analyzer or not, using a light beam or not, and regardless of the liquid being analyzed, wherein that incubator necessitates precise positioning of the held test element along the "Z" axis, that is, along the axis of rotation of the rotor.

Parts and relative positions that are described as being "above", "up" or "down", and the like, refer to orientation and positions that occur during the invention's normal use.

As indicated in the "Background of the Invention", incubators 22 in analyzers such as are shown in U.S. Pat. No. 4,298,571 feature carefully crafted rotors 24, FIG. 1 herein, having precisely machined lower supports 26 that support test elements E thereon at stations such as station A. A cover 28 is releasably pressed onto such test elements by a biasing means such as leaf spring 30, held in the rotor. Body 32 of the rotor includes a ring gear 34 that meshes with and is driven by a gear 36 on a drive shaft 38. Body 32 rotates about a vertical ("Z") axis 40, by means of a bearing 42 that is fixed along axis 40 by reason of shoulder 44 in body 32 and shoulder 46 in the stationary frame 47 of the incubator. The lower support 26 is then caused to rotate or slide above stationary surface 46 of the incubator. That surface and upper stationary surface 48 act to control the temperature of the incubator, as is conventional.

It will be readily appreciated that such a construction requires exact tolerances in the shape of lower support 26, as otherwise it will not be perfectly flat, and will wobble or precess as it turns about axis 40. For uses in which a precise location of a test element E along axis 40 is required, such wobble or precessing error is unacceptable.

In accord with the invention, the precessing error is eliminated without the need for careful rotor tolerances, in the following manner, FIGS. 2 and 3.

Incubator 62 is constructed in a manner similar to that of FIG. 1, that is, to receive and hold colorimetric test elements in a controlled environment at stations such as station A. (As in FIG. 1, means for loading the test elements into the incubator are old, and have been omitted for clarity.) Thus incubator 62 comprises a rotor 64 having a lower rotating support 66 for test elements E that rest thereon, and covers 68 are spring-biased against elements E by leaf springs 70 attached at their inner ends 71 to the rotor body 72. Body 72 is driven by gear 76 and motor 78 driving a ring gear 74, so that rotor 64 rotates about the "Z" axis, 80. A bearing 82 permits rotation of body 72 relative to stationary frame member 87.

In order to allow colorimetric elements E to be read while sandwiched between lower support 66 and cover 68 of rotor 64, a read station 90 is provided, fixed relative to lower surface 86 of the incubator, for example, below it. The station includes a light source 92, and apertures 94 and 96 through lower surface 86 and lower support 66, respectively, to allow a light beam 100 to impinge on element E, as is conventional. Aperture 96 is also shaped to allow a reflected beam 102 to pass to a detector, not shown, at a different angle than beam 100 (for example, 45° and 90°, respectively, to the surface of element E.)

Figure 3:
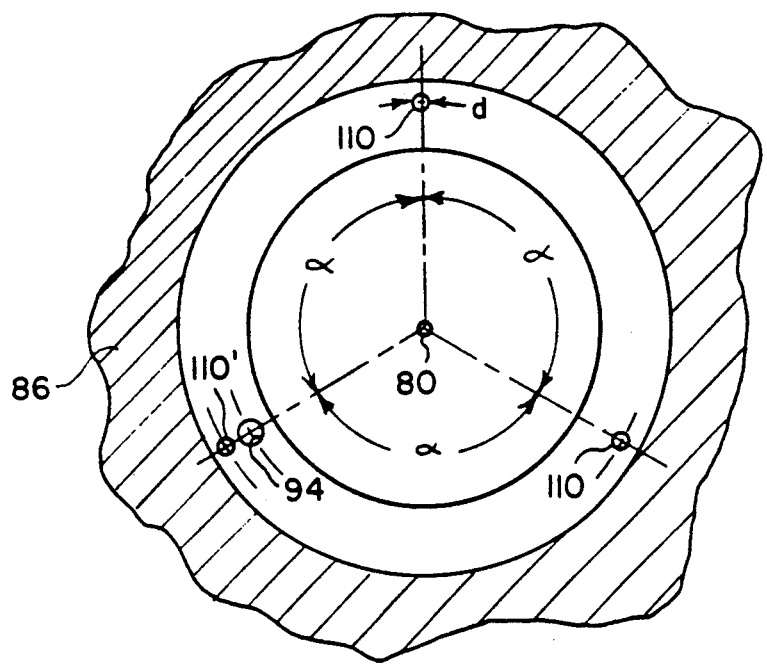
FIG. 3 is a fragmentary plan view of the stationary lower surface of the incubator, to illustrate the preferred spacing of the reference surfaces.

The control of the position of the test element E along the "Z" axis 80 is done, *not* by fixing the location of bearing 82, but rather by providing three reference surfaces 110 on stationary surface 86, FIG. 3, of which one (surface 110') is closely adjacent to aperture 94. Each surface 110 is a bearing surface, against which lower element support 66 slides as the rotor rotates. Surfaces 110 are thus precisely fixed a predetermined distance along axis 80, so as to similarly fix such "Z" axis distance of a test element that passes through light beam 100. (Three surfaces 110 are needed to define a plane.) Because the test element's distance from the read station is thus fixed, bearing 82, fixed to the rotor, is allowed to float vertically on a vertical race 112. Furthermore, lower element support 66 can be manufactured without regard to warpage or not, since it can precess freely as it passes above surface 86 until it makes contact with the reference surfaces 110. In this invention, the thickness of support 66 still needs to be controlled, but this is far easier than controlling overall warpage of support 66.

Preferably, reference surfaces 110 and 110' comprise a pad of a low friction material, such as acetal or nylon materials, and together are less than 5% of the total surface area of surface 86. Most preferably, FIG. 3, reference surfaces 110 and 110' are equally spaced around the circumference of surface 86, each with a diameter "d" of about 9 mm. That is, their angular spacing around axis 80 is at generally equal values of alpha (=120°).

To hold each reference surface 110 and 110' in replaceable position, holes 120 are preferably formed in surface 86, into which the pads are inserted.

Figure 4:
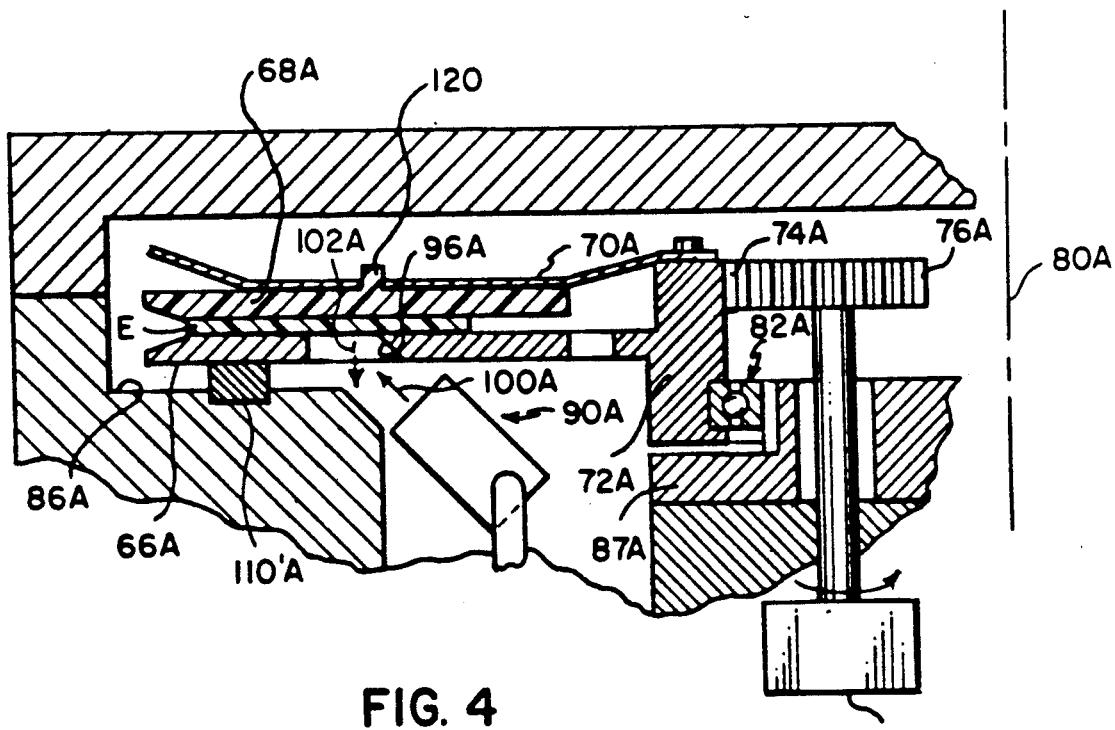
FIG. 4 is an elevational view similar to that of FIGS. 2 and 3, but illustrating an alternate embodiment.
Figure 5:
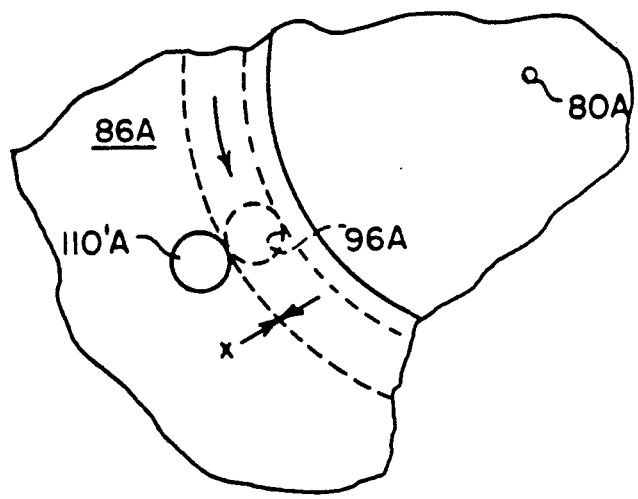
FIG. 5 is an enlarged plan view similar to FIG. 3, but of the embodiment of FIG. 4.

In other embodiments, the driving mechanism for the rotor is mounted inside of body 72, FIG. 4. Parts similar to those previously described bear the same reference numeral, to which the distinguishing suffix "A" is appended. Thus, as in the embodiment of FIG. 4, incubator 62A comprises a rotor 64A that has a lower element support 66A, a cover 68A and a leaf spring 70A releasably pressing cover 68A down onto the test element. Lower support 66A is apertured at 96A to pass a light beam 100A from a light source 92A, and a reflected beam 102A. Rotor body 72A is journalled via bearing 82A that floats vertically on frame 87A. A pin 140 is shown as locating cover 68A relative to spring 70A. As before, reference surface 110'A is located closely adjacent to aperture 96A. A highly preferred construction is one in which the radial distance "X" of surface 110'A measured from where opening 96A passes thereabove approaches zero, FIG. 5. That is, most preferably opening 96A traces an arc that is tangent to the circumference of the pad of surface 110'A.

Figure 2:
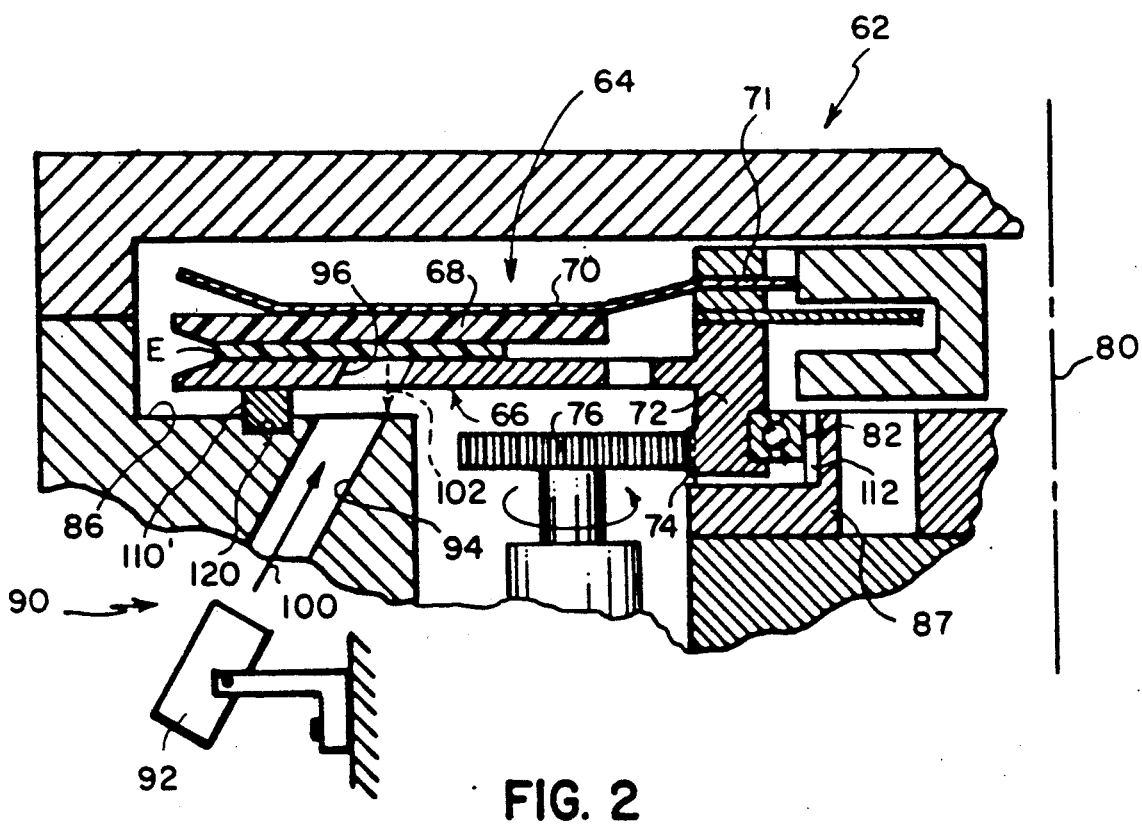
FIG. 2 is an elevational view similar to that of FIG. 1, but illustrating the modification provided by the invention.
Figure 7:
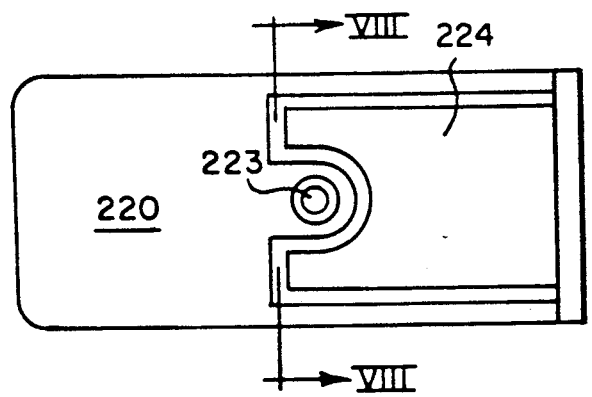
FIG. 7 is a plan view of the spring, cover member and lower support member of the test element holding means.
Figure 8:
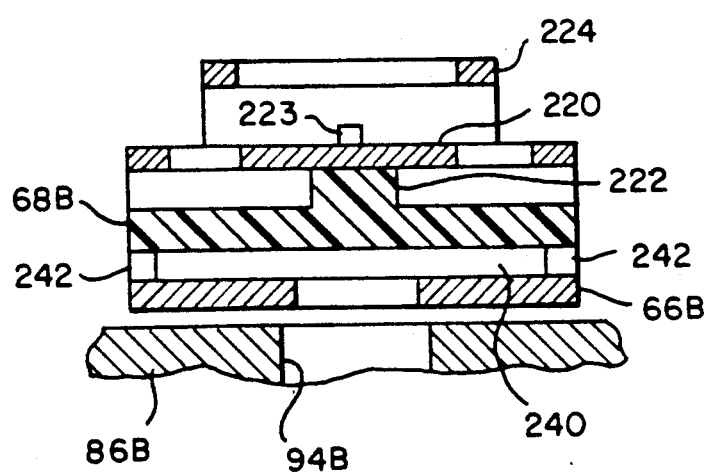
FIG. 8 is a section view taken generally along the line VIII—VIII of FIG. 7, together with the stationary surface of the incubator.

The rotor need not have the configuration shown in FIGS. 2 and 4, but can have a variety of constructions, for example, that shown in FIGS. 6–8. Parts similar to those previously described bear the same reference numeral to which the distinguishing suffix "B" is appended.

Thus, incubator 62B comprises, as before, a rotor 64B which includes a lower support 66B, a cover member 68B and a spring 70B biasing member 68B towards support 66B with a spring force F, to hold a test element E between the two. (Element E is shown as it is being fed inbetween member 68B and support 66B against the spring force F.) Lower support 66B is, as already described, a ring. In this embodiment it is attached by suitable means such as a screw 200, to a flange 202 of rotor 64B. The ring of support 66B slides against three stationary reference pads 110B of which pad 110'B (only one shown) is adjacent to a read aperture 94B in stationary surface 86B, and to read aperture 96B in support 66B.

However, unlike the previous embodiments, spring 70B is a leaf spring mounted so as to be releasibly captured or sandwiched between an upper rotor portion 210 that extends out over much of station A and the spring 70B. Preferably, spring 70B comprises three portions 220, 224 and 240, FIGS. 7 and 8. Portion 220 is a body portion that bears directly onto cover member 68B, specifically a boss 222 thereof, FIG. 8, which has a pin 223 to penetrate portion 220 of spring 70B. Portion 224 is a biasing leg that is stamped out of portion 220, FIGS. 7 and 8, to releasibly fit against portion 210 of rotor 64B, snapped in place behind a ledge 228 of portion 210. Leg 224 also biases body portion 220 downward. An aperture 230 is formed in portion 210, FIG. 6, to allow operator access to flange 224 to depress it to allow the assembly of spring 70B, cover member 68B, and support member 66B to be slid out of the rotor for cleaning and the like. Portion 240 of spring 70B comprises a rear leg that presses against support member 66B. Preferably, both the front and the rear of cover member 68B have a foot 242 at each corner, FIGS. 6 and 8, to raise the cover slightly above an incoming element E, whereby any liquid L, FIG. 6, is not wiped against the cover member.

To drive rotor 64B, gear teeth 260 can be mounted on portion 210, and the rotor is freely journalled at bearing 262 for rotation about a fixed shaft 264. Teeth 260 are engaged by any suitable drive means, not shown, for example, a driven pulley or a gear. Alternatively, portion 210 can be smooth and a belt engages it by friction.

Bearing 262 can be biased downwardly against a conical capture sleeve 263, by means of a compression spring 265 held in place by pin 267. This bias insures that support member 66B will press against pads 110'B.

Optionally, a conventional sensor is mounted at 270 to detect flags 272 on rotor 64B, as a means for sensing which station, such as station A, is at the read station comprising apertures 94B and 96B, and a reflectometer (not shown).

Also optionally, rotor 64B can have vertical reinforcing splines 280 connecting the portions 210 of the rotor in between each of the stations.

The invention has been described in detail with particular reference to preferred embodiments thereof, but it will be understood that variations and modifications can be effected within the spirit and scope of the invention.

What is claimed is:

1. In an incubator for use in an analyzer, said incubator comprising a stationary incubator surface above which test elements are moved while being held in assigned test element stations; a rotor including holding means for holding test elements at said stations; means for rotating said rotor about an axis, including drive means and means for connecting said rotor to said drive means, said connecting means including bearing means for providing relative rotation between said rotor and said stationary surface;

said holding means including a lower support mounted to slide above said stationary surface and a cover member, a test element being sandwichable between said lower support and said cover member; and reading means fixed in said incubator for scanning a test element held in said holding means, one of said lower support and said cover member having an aperture to allow a scanning beam to pass through to a test element held by said holding means;

the improvement wherein said stationary surface includes three reference surfaces comprising a fraction of said stationary surface and positioned a predetermined distance along said axis so to project above said surface, one of said reference surfaces being circumferentially positioned adjacent said aperture to insure proper reading distance for test elements read by said reading means, said lower support being mounted so as to movably bear on said reference surfaces;

and wherein said bearing means is free to move in a direction parallel to said axis, whereby said reference surfaces and not said bearing means determine the distance along said axis of test elements held by said holding means at said read station.

2. An incubator as defined in claim 1, wherein said three reference surfaces are separated at equal distances around the circumference of said stationary surface.

3. An incubator as defined in claim 2, wherein said reference surfaces comprise pads of low friction material, replacably mounted in holes in said stationary surface.

4. An incubator as defined in claim 1, 2 or 3, wherein said rotor includes a spring biasing said cover member towards said lower support.

5. An incubator as defined in claim 4, wherein said spring is a leaf spring having a body portion releasibly pressed against said cover member, and two legs extending from said body portion.

6. An incubator as defined in claim 5, wherein said rotor includes a ledge and one of said legs is constructed to releasibly snap in place relative to said ledge so that said spring is captured by said rotor.

7. An incubator as defined in claim 6, wherein the other of said legs is releasibly pressed against said lower support.

* * * * *